(12) United States Patent
Davis et al.

(10) Patent No.: US 6,248,293 B1
(45) Date of Patent: Jun. 19, 2001

(54) TRAYLINER FOR STERILIZATION PROCESS AND METHOD OF STERILIZING AN ARTICLE

(75) Inventors: Phillip Davis, Weston; Vito L. DiPinto, South Windsor, both of CT (US)

(73) Assignee: General Hospital Supply Corporation, Wilton, CT (US)

( * ) Notice: Subject to any disclaimer, the term of this patent is extended or adjusted under 35 U.S.C. 154(b) by 0 days.

(21) Appl. No.: 09/148,121

(22) Filed: Sep. 4, 1998

(51) Int. Cl.$^7$ ........................................................ A61L 2/20
(52) U.S. Cl. ............................ 422/28; 422/300; 206/370; 206/438
(58) Field of Search ..................................... 422/292, 297, 422/300, 22, 23, 28; 206/370, 523, 557, 438; 428/159

(56) References Cited

U.S. PATENT DOCUMENTS

| | | |
|---|---|---|
| D. 263,076 | 2/1982 | Sandel . |
| D. 263,745 | 4/1982 | Sandel . |
| 4,142,632 | 3/1979 | Sandel . |
| 4,485,919 | 12/1984 | Sandel . |
| 4,671,943 | 6/1987 | Wahlquist . |
| 4,798,292 | 1/1989 | Hauze . |
| 5,098,676 | 3/1992 | Brooks, Jr. . |
| 5,325,987 | 7/1994 | Alpern et al. . |
| 5,340,551 | 8/1994 | Berry, Jr. . |
| 5,389,084 | 2/1995 | Horan et al. . |
| 5,407,648 | 4/1995 | Allen et al. . |
| 5,518,115 | 5/1996 | Latulippe . |
| 5,595,296 | 1/1997 | Wood . |
| 5,667,753 | 9/1997 | Jacobs et al. . |
| 5,792,422 * | 8/1998 | Lin et al. ................................ 422/31 |

OTHER PUBLICATIONS

Dec., 1997, Feldman et al., Compatability of Medical Devices . . . , Medical Devices and Diagnostic Industry.
1998 Brochure for Sterad Sterilization System, Advanced Sterilization Products (7 pages).
1998, Jacobs, Plasma Sterilization, Advanced Sterilization Products website (3 pages).
1998, Plasma, Advanced Sterilization Products website (2 pages).
1997 Brochure for Instrument Trayliner, General Hospital Supply Corporation (1 page).
Brochure for Plasma–Cel Instrument Guards, Cygnus Medical (4 pages).
Brochure for Steri–Cel Instrument Protectors, Cygnus Medical (2 pages).
Brochure for Opcell Foam Plastics, Sentinel Products Corp. (1 page).
Brochure for Cell–Aire Polyethylene Foams, Sealed Air Corporation (1 page).

* cited by examiner

*Primary Examiner*—Elizabeth McKane
(74) *Attorney, Agent, or Firm*—Roger C. Phillips

(57) ABSTRACT

A trayliner for cushioning an article contained in a tray during a sterilization process, the tray including a base having a multiplicity of holes. The trayliner has a multiplicity of holes arranged such that at least a portion of the holes of the trayliner will be generally aligned with at least a portion of the holes of the base of the tray when the trayliner is positioned on the base of the tray. A method of sterilizing an article is also provided and includes positioning a closed cell polyethylene foam plastic trayliner having a multiplicity of holes into a tray, and positioning the article onto the trayliner. The tray containing the trayliner and the article is placed in a sterilization unit, and the sterilization unit is operated. According to one aspect, a base of the tray includes a multiplicity of holes. The method further includes arranging the multiplicity of holes of the trayliner such that at least a portion of the holes of the trayliner will be generally aligned with at least a portion of the multiplicity of holes of the base of the tray when the trayliner is positioned on the base of the tray, and positioning the foam plastic trayliner on the base of the tray such that at least a portion of the holes of the trayliner are generally aligned with at least a portion of the holes of the base.

15 Claims, 2 Drawing Sheets

TRAYLINER FOR STERILIZATION PROCESS AND METHOD OF STERILIZING AN ARTICLE

BACKGROUND

The present disclosure relates, in general, to a trayliner for a sterilization process. Even more particularly, the present disclosure relates to a trayliner for cushioning articles in a low temperature hydrogen-peroxide gas plasma sterilization system.

As is well known, articles used in the health care industry, such as surgical instruments, must be sterilized before and after each use. Many articles, such as fiber optic endoscopes, laser handpieces, power drills and ophthalmic devices, are very delicate and, thus, are preferably cushioned when being sterilized to prevent costly repairs and to reduce down time.

There are generally three sterilization processes for use on surgical equipment: high temperature steam, ethylene oxide, and low temperature hydrogen-peroxide gas plasma. For a number of well-known reasons, hydrogen-peroxide gas plasma sterilization is becoming the preferred sterilization method. For example, hydrogen-peroxide gas plasma sterilization has significantly less corrosive effect on metal surgical instruments, and leaves no residue that may cause the sterilized surgical instruments to be irritating or toxic to patients. In addition, hydrogen-peroxide gas plasma sterilization produces no toxic byproducts and requires no special ventilation or aeration.

A STERRAD® hydrogen-peroxide plasma sterilization system available from Advanced Sterilization Products of Irvine, Calif., for example, is designed to provide non-toxic, dry, low-temperature sterilization in about one hour, without toxic residues. However, the STERRAD® system is not usable with cellulose-based products like linen or paper normally used in other sterilization processes. Cellulose-based products, as well as many other materials commonly used in sterilization, are absorbent and trap fluid during the sterilization process. During hydrogen-peroxide plasma sterilization, absorbent materials can cause an unwanted residue to be left on the articles being sterilized. Thus, the use of such absorbent materials in the hydrogen-peroxide sterilization process requires different cycle parameters to achieve sterilization, without leaving a residue on the article being sterilized, in a fixed cycle of the current design.

The STERRAD™ system includes a sterilization chamber and a tray for holding surgical instruments and articles such as fiber optic endoscopes, laser handpieces, power drills and ophthalmic devices, within the sterilization chamber during the sterilization process. The tray includes a base having a multiplicity of holes for allowing plasma to flow therethrough and contact the article being sterilized during the sterilization process.

One existing trayliner for use with the STERRAD® system is available from Cygnus Medical of Branford, Conn., under the trademark Plasma-Cel™ and consists of a sheet of open cell polyethylene foam. While this trayliner is not cut to the exact dimensions of the tray, the trayliner generally covers the base of the tray of the STERRAD® system to cushion surgical instruments during the sterilization process. The open cell structure of the plastic foam trayliner allows plasma to pass directly through the trayliner, such that the foam trayliner does not interfere with the passage of plasma through the tray holes. While this particular open cell foam trayliner has been found to work with the STERRAD® system, since open cell polyethylene is relatively expensive, the Plasma-Cel™ trayliner typically is reused a number of times to make each individual trayliner cost effective. Thus, users are instructed that they may reuse the Plasma-Cel™ trayliner up to five times. It is unlikely, however, that users feel comfortable with the idea of reusing, and keeping track of the number of uses of, a sterilization trayliner in a sterile hospital environment. Thus, the relatively expensive open cell polyethylene foam trayliners are often disposed of after a single use.

What is still needed, accordingly, is a trayliner for cushioning articles, such as fiber optic endoscopes, laser handpieces, power drills and ophthalmic devices, in a hydrogen-peroxide gas plasma sterilization system. Preferably, the trayliner will have low absorbency, yet will allow the passage of plasma therethrough, such that an article can effectively be sterilized in a hydrogen-peroxide gas plasma sterilization system. In addition, the trayliner will preferably be relatively inexpensive such that disposing of the trayliner after a single use is cost effective.

SUMMARY

Accordingly, a method for sterilizing an article in a hydrogen-peroxide gas plasma sterilization unit is provided. The method includes positioning a closed cell foam plastic trayliner within the sterilization unit, positioning the article onto the trayliner, and operating the hydrogen-peroxide gas plasma sterilization unit.

According to one aspect, the foam plastic is provided as closed cell polyethylene.

According to another aspect, the foam plastic is provided as Cell-Aire® polyethylene foam.

According to an additional aspect, the foam plastic trayliner is provided with a multiplicity of holes.

According to a further aspect, the sterilization unit includes a tray having a base with a multiplicity of holes. The method further includes configuring the foam plastic trayliner with a multiplicity of holes arranged such that at least a portion of the holes of the trayliner will be generally aligned with at least a portion of the holes of the base of the tray when the trayliner is positioned on the base of the tray, and positioning the foam plastic trayliner on the base of the tray such that at least a portion of the holes of the trayliner are generally aligned with at least a portion of the holes of the base. The article to be sterilized is then placed on the trayliner in the tray, and the tray containing the trayliner and the article is placed within the sterilization unit.

According to yet another aspect, the method additionally includes removing the article from the sterilization unit after the article has been sterilized, and disposing of the foam plastic trayliner after a single sterilization process.

Another method of sterilizing an article is provided and includes positioning a closed cell foam plastic trayliner having a multiplicity of holes into a tray, and positioning the article onto the foam plastic trayliner. The tray containing the trayliner and the article is then placed in a sterilization unit, and the sterilization unit is operated.

According to one aspect, the tray includes a base with a multiplicity of holes. The method also includes arranging the multiplicity of holes of the foam plastic trayliner such that at least a portion of the holes of the trayliner will be generally aligned with at least a portion of the holes of the base of the tray when the trayliner is positioned on the base of the tray, and positioning the foam plastic trayliner on the base of the tray such that at least a portion of the holes of the trayliner are generally aligned with at least a portion of the holes of the base.

According to another aspect, the method also includes removing the tray from the sterilization unit after the article has been sterilized, removing the article from the tray, and disposing of the foam plastic trayliner.

A trayliner is provided for cushioning an article contained in a tray including a base having a multiplicity of holes. The trayliner is a closed cell plastic foam and has a multiplicity of holes arranged such that at least a portion of the holes of the trayliner will be generally aligned with at least a portion of the holes of the base of the tray when the trayliner is positioned on the base of the tray.

According to one aspect, the foam plastic comprises closed cell polyethylene.

According to another aspect, the foam plastic is Cell-AireO polyethylene foam.

Still other features and advantages will become apparent upon reading the following detailed description in conjunction with the drawings and the appended claims.

DETAILED DESCRIPTION

Figure 1:
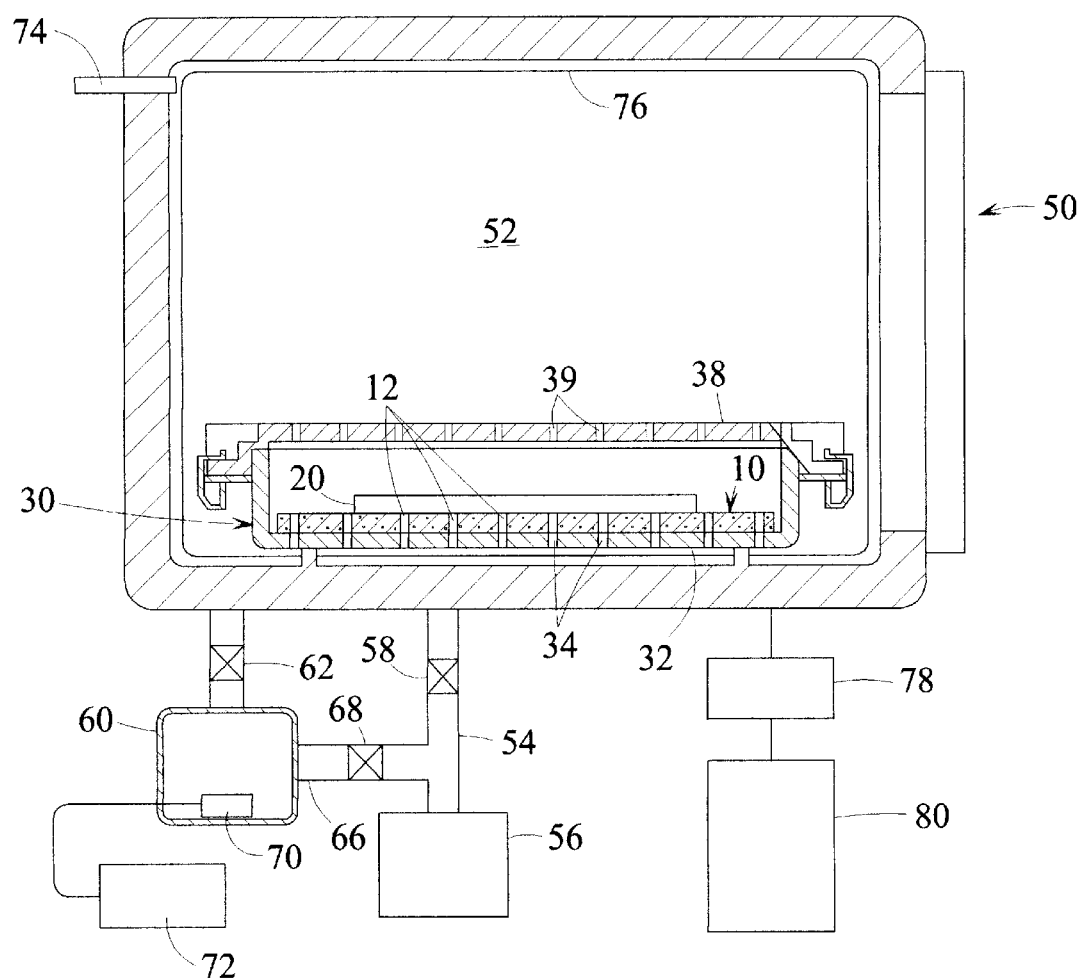
FIG. 1 shows a cross-sectional view of a trayliner cushioning a simplified representation of an article to be sterilized, such as a fiber optic endoscope, laser handpiece, power drill or ophthalmic device, in a somewhat schematic representation of a sterilization unit.
Figure 2:
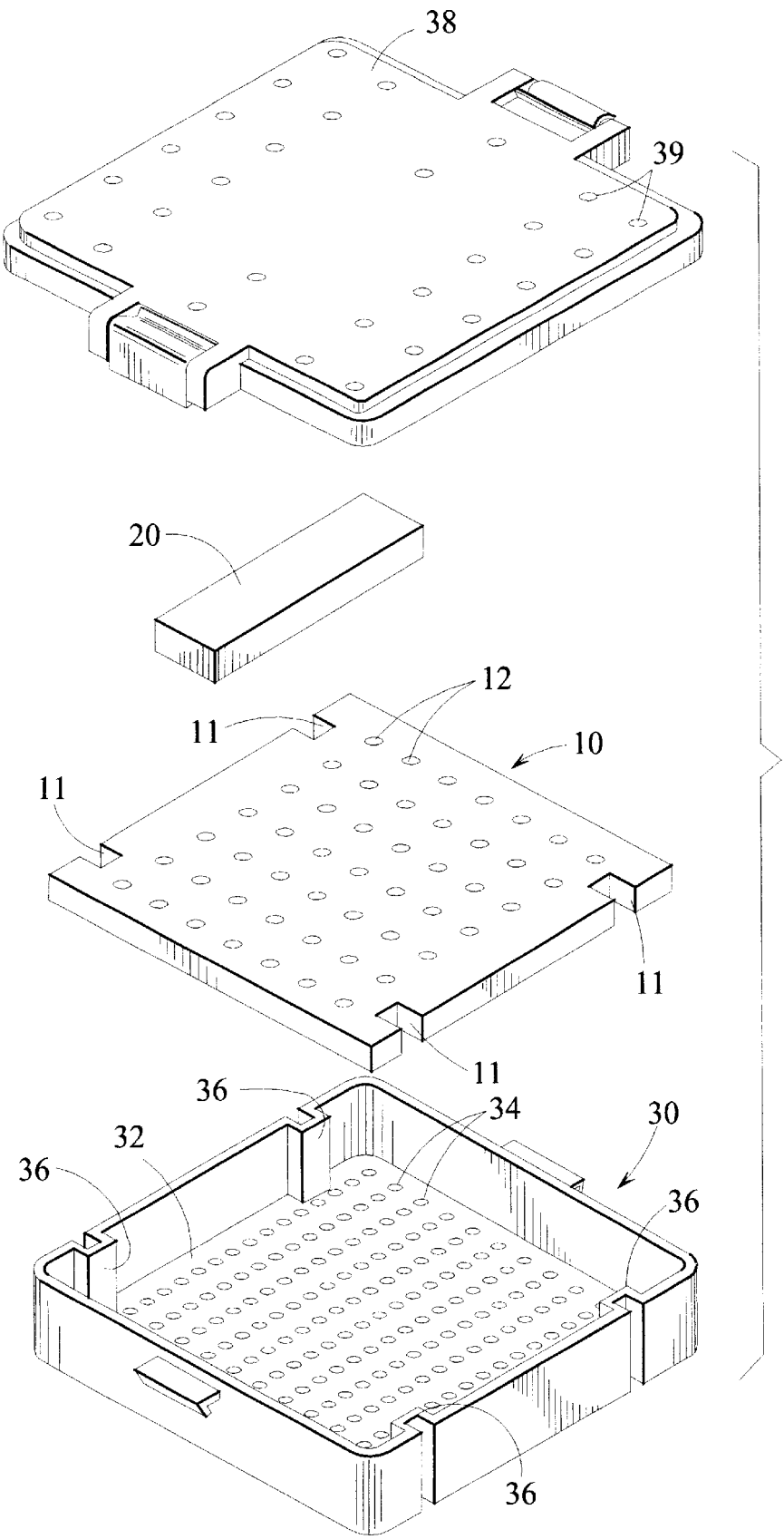
FIG. 2 shows an isometric, exploded view of a tray, the article to be sterilized and the trayliner of FIG. 1.

Referring to FIGS. 1 and 2, a trayliner 10 is provided for cushioning an article 20 to be sterilized, such as a fiber optic endoscope, laser handpiece, power drill or ophthalmic device, during a sterilization process. The trayliner 10 generally comprises a sheet of plastic foam cut to substantially cover a base 32 of a sterilization tray 30. Preferably, the trayliner 10 is cut to the exact dimensions of the base 32 and, in fact, includes notches 11 corresponding to channels 34 in a sidewall 36 of the tray 30.

The trayliner 10 also has a multiplicity of holes 12 arranged such that at least a portion of the holes of the trayliner will be generally aligned with at least a portion of a multiplicity of holes 34 in the base 32 of the sterilization tray 30. The multiplicity of holes 12 in the trayliner 10 allows for the unobstructed passage of a sterilization medium through the tray 30 and the trayliner 10. The number of holes 12 provided in the trayliner 10 may vary, but is generally enough to allow at least a sufficient amount of sterilization medium to circulate within the tray 30 for purposes of sterilization. As illustrated by the particular trayliner 10 shown, the holes 12 are circular and arranged in diagonal rows corresponding to diagonal rows of the circular holes 34 of the tray 30. Preferably, the number of holes 12 of the trayliner 10 is equal to approximately half the number of holes 32 of the tray 30, such that every other hole of the base 32 has a corresponding hole of the trayliner. The arrangement and number of holes 12 in the trayliner 10, however, is ultimately based upon the arrangement and number of holes 32 provided in the tray. As shown, the tray 30 also includes a cover 38 having a multiplicity of holes 39.

The plastic foam of the trayliner 10 preferably has a closed cell construction. A specific closed cell foam suitable for use is Cell-Aired polyethylene foam available from Sealed Air Corporation of Saddle Brook, N.J.

TABLE 1

| Physical Properties | Test Method | CA 20 | CA 30 | CA 60 | CA 90 | CA 125 | CA 185 | CA 250 |
|---|---|---|---|---|---|---|---|---|
| Nominal Thickness | | 1/48" | 1/32" | 1/16" | 3/32" | 1/8" | 3/16" | 1/4" |
| Compressive Strength | ASTM D3575-93 | 1.4 | 2.3 | 2.5 | 2.6 | 2.8 | 2.8 | 2.9 |
| Vertical Direction (psi) | Suffix D @ 25%/50% | 8.0 | 9.5 | 9.6 | 9.8 | 10.0 | 10.4 | 9.6 |
| Compression Set (%) | ASTM D3575-93 Suffix B | 15.5 | 16.8 | 25.0 | 29.0 | 31.9 | 33.7 | 29.8 |
| Tensile Stress (psi) | ASTM D3575-93 | 118 | 106 | 86 | 61 | 62 | 43 | 41 |
| (@ Each Thickness) | Suffix T MD/CMD | 44 | 35 | 29 | 26 | 25 | 24 | 22 |
| Elongation (%) | ASTM D3575-93 | 6 | 8 | 8 | 13 | 18 | 13 | 21 |
| | Suffix T MD/CMD | 2 | 3 | 3 | 3 | 8 | 5 | 8 |
| Tear Resistance (lb/in) | ASTM D3575-93 | 13.6 | 10.9 | 8.8 | 9.0 | 8.5 | 7.4 | 8.3 |
| (@ Each Thickness) | Suffix G MD/CMD | 20.3 | 18.4 | 15.0 | 14.0 | 13.6 | 11.5 | 11.9 |
| Density Range (lb/ft$^3$) | ASTM D3575-93 | 1.35–1.55 | 1.20–1.40 | 1.10–1.30 | 1.10–1.30 | 1.10–1.30 | 1.10–1.30 | 1.10–1.30 |
| Water Absorption (lb/ft$^2$) | ASTM D3575-93 Suffix L | <0.1 | <0.1 | <0.1 | <0.1 | <0.1 | <0.1 | <0.1 |
| Thermal Stability MD/CMD Except Thickness Direction | ASTM D3575-93 Suffix S | <5% | <5% | <5% | <5% | <5% | <5% | <5% |
| Water Vapor Transmission Rate GM/100 In$^2$/24 hr. | ASTM F-1249 | .517 | 0.204 | 0.173 | 0.110 | 0.086 | 0.089 | 0.052 |
| Thermal Resistance R-Value (HR-FT$^2$-° F./BTU) | ASTM C518-91 | 6 Layers 0.77 | 6 Layers 0.90 | 5 Layers 1.03 | 1 Layer 0.47 | 1 Layer 0.53 | 1 Layer 0.89 | 1 Layer 0.86 |
| Thermal Conductivity K-Value (BTU-IN/HR-FT$^2$-° F.) | ASTM C518-91 | 6 Layers 0.20 | 6 Layers 0.23 | 5 Layers 0.25 | 1 Layer 0.19 | 1 Layer 0.21 | 1 Layer 0.25 | 1 Layer 0.20 |
| Static Decay (Anti-Static Grade) | EIA STD. 541 Appendix F | N/A | <2 sec | <2 sec | <2 sec | <2 sec | <2 sec | <2 sec |
| Surface Resistivity (Anti-Static Grade) | EIA STD. 541 Section 4.3 | N/A | $1.0 \times 10^9$– $1.0 \times 10^{12}$ | $1.0 \times 10^9$– $1.0 \times 10^{12}$ | $1.0 \times 10^9$– $1.0 \times 10^{12}$ | $1.0 \times 10^9$– $1.0 \times 10^{12}$ | $1.0 \times 10^9$– $1.0 \times 10^{13}$ | $1.0 \times 10^9$– $1.0 \times 10^{12}$ |
| Flexibility +71° F.–65° F. | PP-C-1752 D | Pass | Pass | Pass | Pass | Pass | Pass | Pass |

TABLE 1-continued

| Physical Properties | Test Method | CA 20 | CA 30 | CA 60 | CA 90 | CA 125 | CA 185 | CA 250 |
|---|---|---|---|---|---|---|---|---|
| Contact Corrosivity (Alum. Plate) | Method 3005 FED STD 101 | None | None | None | None | None | None | None |

Closed cell foam plastic provides many advantages for use in sterilization. For example, closed cell foam plastic is less likely to develop loose particulate material when cut or processed for distribution. This is important of course since loose particulate material is very undesirable within the surgical environment. Also, closed cell foam plastic is relatively easy to sterilize because closed cell foam plastic has few cracks, nooks and crannies and, thus, a sterilization medium such as hydrogen peroxide gas plasma, for example, can more easily reach all surfaces of the closed cell foam plastic and provide sterilization.

The trayliner 10 is particularly adapted for use in a hydrogen-peroxide ($H_2O_2$) gas plasma sterilization system. Advanced Sterilization Products of Irvine, Calif., for example, markets a STERRAD® $H_2O_2$ gas plasma sterilization system. Such systems are becoming increasingly popular by providing a non-toxic, dry, low temperature sterilization process.

FIG. 1 shows a schematic representation of an $H_2O_2$ gas plasma sterilization system 50. Such a system is disclosed in greater detail in U.S. Pat. No. 5,667,753, the disclosure of which is incorporated herein by reference. In general, however, the sterilization system 50 includes a sterilization chamber 52 for containing an article 20 to be sterilized.

For purposes of simplification and generalization, the article 20 to be sterilized is illustrated as a rectangular block. However, it should be understood that the article 20 can comprise any medical device requiring sterilization before and after each use, and, in particular, delicate surgical devices, such as fiber optic endoscopes, laser handpieces, power drills and ophthalmic devices, that are preferably cushioned when being sterilized to prevent costly repairs and to reduce down time.

The chamber 52 of the sterilization system 50 includes an outlet 54 leading to a vacuum pump 56 for evacuation of the chamber. The outlet 54 includes a valve 58 for isolating the chamber 52 from the pump 56. The chamber 52 also includes an inlet 60, containing a valve 62, that is connected to an enclosure 64 containing hydrogen peroxide. A conduit 66 having a valve 68 connects the $H_2O_2$ enclosure 64 to the vacuum pump 56. The enclosure 64 contains a heater 70 attached to a temperature controller 72, while the chamber 52 includes a peroxide monitor 74. The chamber 52 also includes a radio frequency (RF) electrode 76, to which is attached a matching network 78 and an RF power supply 80.

Operation of the $H_2O_2$ gas plasma sterilization system 50 includes opening valve 62 to allow $H_2O_2$ vapor from the enclosure 64 to be delivered into the chamber 52. The $H_2O_2$ may be heated by the heater 70 in the enclosure 64 to facilitate the release of the $H_2O_2$ vapor. Air or inert gas may also be added to the $H_2O_2$ vapor. The article 20 to be sterilized is either treated with peroxide vapor until sterilized or pretreated with peroxide vapor in the chamber 52 before plasma with sufficient power to sterilize is generated.

The chamber 52 may then be evacuated to facilitate generation of the plasma. The article 20 is subject to a plasma by applying power from the RF power supply 80 to the RF electrode 76. The article 20 remains in the plasma for a period sufficient to effect complete sterilization and/or to remove residual $H_2O_2$.

The term "plasma" is intended to include any portion of the gas or vapor that contains electrons, ions, free radicals, dissociated and/or excited atoms or molecules produced as a result of an applied electric field, including any accompanying radiation that might be produced.

A preferred method for sterilizing an article 20 includes positioning the closed cell foam plastic trayliner 10 having the multiplicity of holes 12 into the tray 30, as shown in FIG. 2, and positioning the article 20 on the trayliner. The tray 30 containing the trayliner 10 and the article 20 is then placed in the sterilization unit 50, as shown in FIG. 1, and the sterilization unit is operated as the unit normally would be until the article is sterilized.

The method may further include arranging the multiplicity of holes 12 in the foam plastic trayliner 10 such that, at least a portion of the holes of the trayliner will be generally aligned with at least a portion of the multiplicity of holes 34 of the base 32 of the tray 30. The foam plastic trayliner 10 is then positioned on the base 32 of the tray 30 such that at least a portion of the holes 12 of the trayliner are generally aligned with at least a portion the holes 34 of the base, as shown in FIGS. 1 and 2, whereby the trayliner does not interfere with the passage of the sterilization medium through the holes of the tray. Preferably, the number of holes 12 of the trayliner 10 equals approximately half the number of holes 32 of the tray 30, such that the holes of the trayliner correspond to every other hole of the tray.

The method may also include removing the tray 30 from the sterilization unit 50, after the sterilization unit has finished a normal sterilization cycle, and removing the then sterilized article 20 from the tray. The foam plastic trayliner 10 is then preferably disposed of in a proper waste container after the single sterilization process.

The principles, preferred embodiments and modes of operation of the present trayliner have been described in the foregoing specification. The presently disclosed trayliner, however, is not to be construed as limited to the particular embodiment shown as this embodiment is regarded as illustrious rather than restrictive. Moreover, variations and changes may be made by those skilled in the art without departing from the spirit of the presently disclosed trayliner as set forth by the following claims.

What is claimed is:

1. A method for sterilizing an article in a hydrogen-peroxide gas plasma sterilization unit wherein the article is treated within a sterilization chamber of the unit with a hydrogen-peroxide vapor, the method comprising:

positioning a trayliner fabricated from a closed cell, foam material within the sterilization chamber of the sterilization unit, the closed cell material having a percent elongation as determined under ASTM D3575-93 that is within the range of between about two percent and about twenty-one percent;

positioning the article on the trayliner, such that the article is cushioned within the chamber; and operating the hydrogen-peroxide gas plasma sterilization unit such that the article on the trayliner is treated with the hydrogen-peroxide vapor.

2. The method of claim 1 wherein the closed cell, foam material has a compression strength as determined under ASTM D3575-93 that is within the range of between about 1.4 psi at twenty five percent deflection and about 2.9 psi at twenty five percent detection.

3. The method of claim 1 wherein the closed cell, foam material has a compression strength as determined under ASTM D3575-93 that is within the range of between about 8 psi at fifty percent deflection and about 10.4 psi at fifty percent deflection.

4. The method of claim 1 wherein the trayliner is provided with a multiplicity of holes.

5. The method of claim 1 wherein the hydrogen-peroxide gas plasma sterilization unit includes a tray with a base having a multiplicity of holes, the method further comprising;

configuring the trayliner with a multiplicity of holes such that at least a portion of the holes of the trayliner will be generally aligned with at least a portion of the multiplicity of holes of the base of the tray when the trayliner is positioned on the base of the tray;

positioning the trayliner on the base of the tray such that at least a portion of the holes of the trayliner are generally aligned with at least a portion of the holes of the base of the tray; and positioning the tray containing the trayliner and the article within the sterilization unit.

6. The method of claim 1 further comprising:

removing the article from the sterilization unit after the article has been sterilized; and disposing of the trayliner.

7. A method of sterilizing an article comprising:

positioning a trayliner fabricated from a closed cell, foam material into a tray for cushioning the article, the closed cell, foam material having a percent elongation as determined under ASTM D3575-93 that is within the range of between about two percent and about twenty-one percent;

providing a multiplicity of holes in the trayliner for allowing a sterilizing medium to pass therethrough;

positioning the article on the trayliner;

positioning the tray containing the trayliner and the article in a sterilization unit; and operating the sterilization unit for a sufficient period to sterilize the article on the trayliner.

8. The method of claim 7 wherein a base of the tray is configured with a multiplicity of holes, the method further comprising:

configuring the holes of the trayliner such that at least a portion of the holes of the trayliner will be generally aligned with at least a portion of the multiplicity of holes of the base of the tray when the trayliner is positioned on the base of the tray; and positioning the trayliner on the base of the tray such that at least a portion of the holes of the trayliner are generally aligned with at least a portion of the holes of the base of the tray.

9. The method of claim 8 further comprising:

removing the tray from the sterilization unit after the article has been sterilized;

removing the sterilized article from the tray; and disposing of the trayliner.

10. A trayliner for lining a tray, the tray including a base having a multiplicity of holes, the trayliner comprising a sheet fabricated from a closed cell, foam material having a percent elongation as determined under ASTM D3575-93 that is within the range of between about two percent and about twenty-one percent and said sheet having a multiplicity of holes arranged such that at least a portion of the holes of the trayliner will be generally aligned with at least a portion of the multiplicity of holes of the base of the tray when the trayliner is positioned on the base of the tray.

11. The trayliner of claim 10 wherein the closed cell, foam material has a compression strength as determined under ASTM D3575-93 that is within the range of between about 1.4 psi at twenty five percent deflection and about 2.9 psi at twenty five percent deflection.

12. The trayliner of claim 10 wherein the closed cell, foam material has a compression strength as determined under ASTM D3575-93 that is within the range of between about 8 psi at fifty percent deflection and about 10.4 psi at fifty percent deflection.

13. A trayliner for lining a tray of a hydrogen-peroxide gas plasma sterilization unit such that an article contained in the tray is cushioned, the tray including a base having a multiplicity of holes for allowing hydrogen-peroxide vapor and plasma to pass therethrough to sterilize the article and allowing liquid hydrogen-peroxide to drain therefrom, the trayliner comprising;

a sheet fabricated from a closed cell foam material having a density as determined under ASTM D3575-93 that is within the range of between 1.10 pounds per cubic foot and about 1.55 pounds per cubic foot for cushioning the article, the sheet being provided in substantially the same size and shape as the base of the tray;

the sheet having a multiplicity of holes arranged such that at least a portion of the holes of the trayliner will be generally aligned with at least a portion of the multiplicity of holes of the base of the tray when the trayliner is positioned on the base of the tray, whereby hydrogen-peroxide vapor and plasma will be allowed to pass through the tray and the trayliner to sterilize the article and liquid hydrogen-peroxide is allowed to drain from the tray.

14. The trayliner of claim 13 wherein the closed cell, foam material has a compression strength as determined under ASTM D3575-93 that is within the range of between about 1.4 psi at twenty five percent deflection and about 2.9 psi at twenty five percent deflection.

15. The trayliner of claim 13 wherein the closed cell, foam material has a compression strength as determined under ASTM D3575-93 that is within the range of between about 8 psi at fifty percent deflection and about 10.4 psi at fifty percent deflection.

\* \* \* \* \*